(12) United States Patent
Crosby et al.

(10) Patent No.: US 9,108,053 B2
(45) Date of Patent: Aug. 18, 2015

(54) APPARATUS AND METHODS FOR REHABILITATING A MUSCLE AND ASSESSING PROGRESS OF REHABILITATION

(71) Applicant: Mainstay Medical Limited, Dublin (IE)

(72) Inventors: Peter Andrew Crosby, Minneapolis, MN (US); Prashant Brijmohansingh Rawat, Blaine, MN (US)

(73) Assignee: Mainstay Medical Limited, Swords, County Dublin (IE)

( * ) Notice: Subject to any disclaimer, the term of this patent is extended or adjusted under 35 U.S.C. 154(b) by 0 days.

(21) Appl. No.: 13/718,806

(22) Filed: Dec. 18, 2012

(65) Prior Publication Data

US 2014/0058476 A1  Feb. 27, 2014

Related U.S. Application Data

(60) Provisional application No. 61/577,448, filed on Dec. 19, 2011.

(51) Int. Cl.
*A61N 1/36* (2006.01)
(52) U.S. Cl.
CPC .................................. *A61N 1/36003* (2013.01)
(58) Field of Classification Search
CPC .................................................. A61N 1/36003
USPC ...................................................... 607/45–46
See application file for complete search history.

(56) References Cited

U.S. PATENT DOCUMENTS

| 3,077,884 | A | 2/1963 | Batrow et al. |
| 3,893,463 | A | 7/1975 | Williams |
| 4,026,301 | A | 5/1977 | Friedman et al. |
| 4,342,317 | A | 8/1982 | Axelgaard |
| 4,408,609 | A | 10/1983 | Axelgaard |
| 4,658,835 | A | 4/1987 | Pohndorf |
| 5,069,680 | A | 12/1991 | Grandjean |
| 5,199,430 | A | 4/1993 | Fang et al. |
| 5,501,452 | A | 3/1996 | Halvorson |

(Continued)

FOREIGN PATENT DOCUMENTS

| EP | 0 587 269 B1 | 12/1998 |
| WO | WO 2006/133445 A2 | 12/2006 |

(Continued)

OTHER PUBLICATIONS

PCT International Search Report and Written Opinion dated Apr. 5, 2013 in related PCT Application No. PCT/US2012/070259.

(Continued)

*Primary Examiner* — Amanda Patton
(74) *Attorney, Agent, or Firm* — Foley & Lardner LLP; Christopher C. Bolten; Nicola A. Pisano

(57) ABSTRACT

Apparatus and methods for rehabilitating a muscle are provided including one or more electrodes configured to be positioned in or adjacent to tissue, one or more sensors configured to sense muscle contraction and to generate a sensor signal based on the muscle contraction, and a pulse generator operatively coupled to the one or more electrodes, e.g., via a lead, and having a controller configured to receive the sensor signal and to adjust the stimulation frequency based on the sensor signal to cause the muscle to contract where muscle contraction is smooth and continuous.

21 Claims, 6 Drawing Sheets

(56) References Cited

U.S. PATENT DOCUMENTS

| | | |
|---|---|---|
| 5,507,788 A | 4/1996 | Lieber |
| 5,522,854 A | 6/1996 | Ideker et al. |
| 5,733,307 A | 3/1998 | Dinsdale |
| 5,807,234 A | 9/1998 | Bui et al. |
| 5,916,172 A | 6/1999 | Hodges et al. |
| 6,104,957 A | 8/2000 | Alo et al. |
| 6,119,516 A | 9/2000 | Hock |
| 6,319,241 B1 | 11/2001 | King et al. |
| 6,406,421 B1 | 6/2002 | Grandjean et al. |
| 6,516,227 B1 | 2/2003 | Meadows et al. |
| 6,671,557 B1 | 12/2003 | Gliner |
| 6,839,594 B2 | 1/2005 | Cohen et al. |
| 7,206,641 B2 | 4/2007 | Ignagni et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,444,181 B2 | 10/2008 | Shi et al. |
| 7,489,561 B2 | 2/2009 | Armstrong et al. |
| 7,499,746 B2 | 3/2009 | Buhlmann et al. |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,930,039 B2 | 4/2011 | Olson |
| 8,170,690 B2 | 5/2012 | Morgan et al. |
| 2001/0053885 A1 | 12/2001 | Gielen et al. |
| 2002/0161415 A1 | 10/2002 | Cohen et al. |
| 2004/0030360 A1 | 2/2004 | Eini et al. |
| 2004/0111118 A1 | 6/2004 | Hill et al. |
| 2004/0236383 A1 | 11/2004 | Yelizarov |
| 2005/0283204 A1 | 12/2005 | Buhlmann et al. |
| 2006/0111746 A1 | 5/2006 | Foreman et al. |
| 2006/0235484 A1 | 10/2006 | Jaax et al. |
| 2007/0027501 A1 | 2/2007 | Jensen et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0208392 A1 | 9/2007 | Kuschner et al. |
| 2008/0167698 A1 | 7/2008 | Kim et al. |
| 2008/0183221 A1 | 7/2008 | Burdulis |
| 2008/0228241 A1 | 9/2008 | Sachs |
| 2009/0210041 A1 | 8/2009 | Kim et al. |
| 2009/0259280 A1 | 10/2009 | Wilkin et al. |
| 2010/0036454 A1 | 2/2010 | Bennett et al. |
| 2010/0174240 A1 | 7/2010 | Wells et al. |
| 2011/0224665 A1 | 9/2011 | Crosby et al. |
| 2011/0224682 A1 | 9/2011 | Westlund et al. |
| 2012/0035953 A1 | 2/2012 | Armstrong |

FOREIGN PATENT DOCUMENTS

| | | |
|---|---|---|
| WO | WO 2009/134475 A1 | 11/2009 |
| WO | WO-2011/079866 A1 | 7/2011 |

OTHER PUBLICATIONS

Gondin et al., "Electromyostimulation Training Effects on Neural Drive and Muscle Architecture", Medicine & Science in Sports & Exercise 37, No. 8, pp. 1291-1299 (Aug. 2005).

Lieber, Richard L. "Skeletal muscle adaptability. II: Muscle properties following spinal-cord injury", Developmental Medicine and Child Neurology 28, No. 4, pp. 533-542 (Aug. 1986).

Lieber, Richard L. "Skeletal muscle adaptability. III: Muscle properties following chronic electrical stimulation", Developmental medicine and child neurology 28, No. 5, pp. 662-670 (Oct. 1986).

Lieber, Richard L. "Comparison between animal and human studies of skeletal muscle adaptation to chronic stimulation", Clinical Orthopaedics and related research, No. 233, pp. 19-24 (1988).

Rosatelli et al., "Three-dimensional study of the musculotendinous architecture of lumber multifidus and its functional implications", Clinical Anatomy 21, No. 6, pp. 539-544 (Sep. 2008).

APPARATUS AND METHODS FOR REHABILITATING A MUSCLE AND ASSESSING PROGRESS OF REHABILITATION

I. CROSS-REFERENCE TO RELATED APPLICATIONS

This application claims the benefit of priority of U.S. Provisional Application Ser. No. 61/577,448, filed Dec. 19, 2011.

II. FIELD OF THE INVENTION

This application generally relates to diagnosis and assessment of the physiological state of a muscle subject to electrical stimulation to effect rehabilitation, and apparatus and method to monitor progress of rehabilitation.

III. BACKGROUND OF THE INVENTION

Skeletal muscles consist of a number of specialized elongated cells mechanically coupled together. A nerve fiber connects to the muscle cells at a region called the end plate. The combination of the muscle cell or group of cells and the nerve fiber that innervates it is called a motor unit. Motor units come in different sizes, with larger motor units producing greater force than smaller motor units. When a muscle contracts, an electrical signal travels down the nerve fiber and causes depolarization of the cell wall of the muscle fiber, thus triggering biochemical processes inside the muscle cell that generate a twitch of contraction and force generation.

In normal physiology, where nerve signals cause muscle contraction, the force of contraction of a muscle is regulated by the number of motor units that are activated, the size of the motor units, and the frequency of nerve impulses delivered to the motor unit. In general, the nervous system activates smaller motor units first to allow fine control of force, and as the force requirement increases, larger motor units are gradually added.

External electrical stimulation for causing muscle contraction has been known since Galvani observed such contraction in frogs in 1791. Over time, it became known that the most energy efficient way to electrically stimulate a muscle to cause contraction is to stimulate the nerve fiber of the motor unit because the energy required to stimulate a nerve fiber to elicit contraction is about 1000 times less than required to stimulate a muscle to elicit contraction.

If an electrical stimulation electrode is placed on the nerve that supplies the muscle, then a single electrical pulse will cause a single contraction of the muscle referred to as a twitch. The force in the muscle rises rapidly and decays more slowly to zero.

If additional stimulation pulses are applied, additional twitches are produced. If the rate of stimulation is such that a new stimulation pulse is presented before the prior twitch has decayed, then the new twitch will be largely superimposed on the prior, producing a summation of force. As the stimulation rate is increased, this summation of force is such that the twitches blend together to generate a smooth contraction. The stimulation frequency at which the force production transitions from intermittent (rapid twitching) to smooth contraction is often referred to as the fusion frequency. Stimulation at a rate at or above the fusion frequency leads to smooth force generation. In general terms, stimulation at a rate significantly higher than the fusion frequency has minimal effect on the strength or nature of contraction (but may have an adverse impact on fatigue of the muscle). Stimulation at a frequency higher than necessary to achieve the desired (e.g., maximum) force is energy inefficient, which is an important consideration for an implantable device.

The amount of muscle that contracts (and hence the force of contraction) in the twitch is determined primarily by the number of motor units that are stimulated. With electrical stimulation, the strength of the force may be controlled by altering the intensity of the electrical stimulation—in general, higher stimulus intensity will elicit higher force. As the stimulation intensity is increased, then more motor units are recruited to contribute to the force generation.

Muscles responsible for different types of action may have different physiological architecture. Muscles fibers may be classified as generally Type I slow twitch or Type II fast twitch. The classification refers to the speed of contraction and decay of force of an isolated muscle fiber when electrically stimulated. Type I slow twitch muscles are sometimes referred to as "endurance muscles" such as the muscles in the back that keep the spinal column stable or the flight muscles of birds. Type II fast twitch muscles are generally voluntary muscles that are responsible for rapid movement of a joint or fine voluntary control such as hand movements. There are biochemical and histological differences between the muscle types and in particular the energy metabolic pathways of the muscles.

It has been observed that Type I slow twitch muscles that suffer from disuse atrophy over time may change to more Type II fast twitch motor units in the muscle—that is, the muscle becomes less fatigue resistant. As this atrophied muscle is rehabilitated, it is possible that over time the cell type again reverts from Type II fast twitch to predominantly Type I slow twitch, thereby improving the muscle's fatigue resistance. See, e.g., Lieber, Richard L. "Skeletal muscle adaptability. II: Muscle properties following spinal-cord injury", Developmental Medicine and Child Neurology 28, No. 4, pp. 533-42 (August 1986).

One goal of clinical rehabilitation of muscles to restore normal muscle function by for example, physiotherapy and exercise. Rehabilitation is required, for example, during recovery from surgery, after an injury, or following a prolonged period of bed rest. Ideally, rehabilitation of atrophied endurance muscles would also result in reversion of muscle fiber type to Type I slow twitch fibers. It is difficult to determine muscle fiber type without performing a biopsy, which is an invasive procedure. It is an object of the present invention to satisfy an unmet clinical need to provide a diagnostic apparatus and a method to determine muscle fiber type without requiring a biopsy.

Functional electrical stimulation (FES) is the application of electrical stimulation to cause muscle contraction to re-animate limbs following damage to the nervous system such as with stroke or spine injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and the control system for each muscle as well as the system as a whole to produce the desired action such as standing and walking.

With normal physiology, sensors in the muscle, ligaments, tendons and other anatomical structures provide information such as the force a muscle is exerting or the position of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle.

For example, in U.S. Pat. No. 6,839,594 to Cohen, a plurality of electrodes are used to activate selected groups of axons in a motor nerve supplying a skeletal muscle in a spinal cord patient (thereby achieving graduated control of muscle force) and one or more sensors such as an accelerometer are used to sense the position of limbs along with electrodes attached to muscles to generate an electromyogram (EMG) signal indicative of muscle activity. In another example, U.S. Pat. No. 6,119,516 to Hock, describes a biofeedback system, optionally including a piezoelectric element, which measures the motions of joints in the body. Similarly a piezoelectric crystal may be used as a muscle activity sensor as described by U.S. Pat. No. 5,069,680 to Grandjean.

Spinal cord injured patients are sometimes subject to tremor—uncontrolled twitching of muscles in the absence of neural input. The Cohen patent, described above, discloses an apparatus and method for detecting a tremor by way of sensors, e.g., accelerometers or sensing electrodes, and then applying electrical signals to the motor nerve to modify the tremor, the whole system being controlled by a feedback loop.

FES has also been used to treat spasticity, characterized by continuous increased muscle tone, involuntary muscle contractions, and altered spinal reflexes which leads to muscle tightness, awkward movements, and is often accompanied by muscle weakness. Spasticity results from many causes including cerebral palsy, spinal cord injury, trauma, and neurodegenerative diseases. U.S. Pat. No. 7,324,853 to Ayal describes apparatus and method for electrically stimulating nerves that supply muscles to modify the muscle contractions that lead to spasticity. The apparatus includes a control system configured to analyze electrical activity of one or more muscles, limb motion and position, and mechanical strain in an anatomical structure.

Neuromuscular Electrical Stimulation (NMES) is a subset of the general field of electrical stimulation for muscle contraction, as it is generally applied to nerves and muscles which are anatomically intact, but malfunctioning is a different way. NMES may be delivered via an external system or, in some applications, via an implanted system.

NMES via externally applied skin electrodes has been used to rehabilitate skeletal muscles after injury or surgery in the associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al. "Electromyostimulation Training Effects on Neural Drive and Muscle Architecture", Medicine & Science in Sports & Exercise 37, No. 8, pp. 1291-99 (August 2005).

An implanted NMES system has been used to treat incontinence by stimulating nerves that supply the urinary or anal sphincter muscles. For example, U.S. Pat. No. 5,199,430 to Fang describes implantable electronic apparatus for assisting the urinary sphincter to relax.

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

One of the challenges of NMES for rehabilitation of atrophied skeletal muscles is to diagnose when the therapy has been successful and may be discontinued. This is particularly important with patients who cannot communicate, e.g., children, or patients who do not want to communicate, e.g., malingerers who may be motivated for the therapy to not be successful as it would result in loss of workman's compensation insurance.

It would therefore be desirable to provide an apparatus and method to objectively diagnose when rehabilitation of a skeletal muscle has been attained.

Chronic electrical stimulation of Type II fast twitch muscles may result in a gradual change in the fiber type from Type II fast twitch to Type I slow twitch. See, e.g, Lieber, Richard L. "Comparison between animal and human studies of skeletal muscle adaptation to chronic stimulation", Clinical Orthopaedics and related research, No. 233, pp. 1924 (1988); see also, e.g., Lieber, Richard L. "Skeletal muscle adaptability. III: Muscle properties following chronic electrical stimulation", Developmental medicine and child neurology 28, No. 5, pp. 662-70 (October 1986).

Electrical stimulation of muscle via externally applied skin electrodes has been used for strength training and rehabilitation. Conventional methods of such muscle rehabilitation are "open loop." That is, there is no feedback (other than through the clinical practitioner) to determine the effectiveness and progress of the therapy, and to adjust the therapeutic parameters if necessary to achieve the desired outcome. An alternative approach, described in U.S. Pat. No. 7,499,746 to Buhlmann, involves an extracorporeal adaptive muscle stimulation system wherein stimulation delivered via electrodes applied externally to the skin may be adjusted dependent on a detected muscle response to account for muscle fatigue during the therapy session.

It would be advantageous to provide implantable apparatus for closed loop control of a NMES system, data logging of the progress of therapy, and capable of adjusting other parameters as the therapy progresses over multiple sessions, and methods of using the same.

These advantages accrue strongly for an implanted NMES system, designed for example for muscle rehabilitation or muscle control. U.S. Patent Application Publication No. 2008/0228241 to Sachs and U.S. Patent Application Publication No. 2011/0224665 to Crosby, both assigned to the assignee of the present invention, and both incorporated herein in their entireties by reference, describe implanted electrical stimulation devices that are designed to restore neural drive and rehabilitate muscle such as the abdominal multifidus muscle to improve stability of the spine.

The multifidus is a complex muscle with many fascicles, with deeper fascicles composed of primarily slow twitch fibers responsible for stability of the lumbar spine. See, e.g., Rosatelli et al., "Three-dimensional study of the musculotendinous architecture of lumbar multifidus and its functional implications", Clinical Anatomy 21, No. 6, pp. 539-44 (September 2008). It is known that when the normal physiological motor control system that drives the multifidus is disrupted and the multifidus atrophies, the muscle fiber type converts from Type I slow twitch to Type II fast twitch fibers.

It would be desirable to provide a system for monitoring and recording progress of NMES for rehabilitation of a muscle, for example, the lumbar multifidus muscle. It further would be desirable to provide a system to adjust the operating parameters of a NMES system based on measurement of muscle performance, thereby continually optimizing the NMES system.

It also would be desirable to provide an implantable system that utilizes the lowest stimulation frequency consistent with the therapeutic requirements, thereby preserving battery life.

IV. SUMMARY OF THE INVENTION

The present invention overcomes the drawbacks of previously-known systems by providing apparatus and methods for rehabilitating a muscle or muscles, e.g., a skeletal muscle and/or muscles associated with local segmental control of the spine. The apparatus may include one or more electrodes, one or more sensors, and a pulse generator. The electrodes are configured to be positioned in or adjacent to tissue and to stimulate the tissue at a stimulation frequency and at a level and duration sufficient to cause the target muscle(s) to contract. The sensors are configured to sense the muscle contraction and to generate a sensor signal based on the muscle contraction. The pulse generator is operatively coupled to the one or more electrodes, e.g., via a lead. The pulse generator includes a controller configured to receive the sensor signal and to adjust the stimulation frequency based on the sensor signal.

Advantageously, the stimulation frequency may be periodically or continuously adjusted to be at or above a fusion frequency to cause the muscle to contract over the course of treatment to enhance rehabilitation of the muscle. In accordance with one aspect of the present invention, the controller of the pulse generator is configured to sweep through a range of stimulation frequencies to identify the fusion frequency for the targeted muscle. As defined herein, the fusion frequency is that frequency at which electrical stimulation of the muscle results in smooth continuous contraction of the muscle, rather than rapid, twitching contractions. The controller may be configured to adjust the stimulation frequency over a course of a therapy to reflect changes in the fusion frequency of the muscle resulting from prior therapeutic stimulation sessions. In accordance with the principles of the present invention, prolonged stimulation of the targeted muscle at the fusion frequency may contribute to conversion of Type II fast twitch fibers to Type I slow twitch fibers.

The one or more electrodes may be configured to be implanted, temporarily or permanently, in or adjacent to various tissue including nerve, muscle, ligament, and/or joint capsule. In one embodiment, the muscle to be contracted is the multifidus muscle and the electrodes are implanted in or adjacent to the medial branch of the dorsal ramus nerve which innervates the multifidus muscle. By way of example, stimulation is of the medial branch of the dorsal ramus that exits between the L2 and L3 lumbar segments and passes over the transverse process of the L3 vertebra, thereby eliciting contraction of fascicles of the lumbar multifidus at the L3, L4, L5 and S1 segments and in some patients also at the L2 segment. In another embodiment, the electrodes are placed superficially on the skin over or adjacent to the target muscle and connected to an external pulse generator.

The one or more sensors may be at least one of an accelerometer, a pressure sensor, a movement sensor, a strain gauge, or any combination thereof. The sensors may be disposed within a housing of the pulse generator or disposed in any suitable location for sensing muscle contraction such as within or adjacent to the tissue and/or muscle to be contracted, or as part of the lead system within or adjacent to the muscle.

The pulse generator may be a permanent or temporary implantable pulse generator (IPG) configured to be implanted in a body or, alternatively, may be configured to be disposed external to a body.

The controller of the pulse generator is programmable and may be programmed to automatically adjust the stimulation frequency based on the sensor signal. The controller further may adjust the stimulation frequency based on the sensor signal to determine a fusion frequency of the muscle. In one embodiment, the controller determines the fusion frequency by processing a sensor signal from the sensor indicating that muscle movement/acceleration during muscle contraction is at or near zero. The controller may be programmed to direct the one or more electrodes to stimulate the tissue below, at or above the fusion frequency.

The apparatus may wirelessly transmit data to and receive data from an external system that may be coupled, either wirelessly or using a cable, to a user's or physician's computer to download for review data stored on the pulse generator, or to adjust the stimulation parameters of the pulse generator.

In accordance with one aspect of the present invention, a method for rehabilitating a muscle is provided. The method includes positioning one or more electrodes in or adjacent to tissue; using the one or more electrodes to stimulate the tissue at a stimulation frequency and at a level and duration sufficient to induce smooth and continuous contraction of the muscle; sensing the muscle contraction; and adjusting the stimulation frequency to maintain smooth and continuous muscle contraction.

The method may further include providing a sensor configured to detect a predetermined orientation of a patient's body and delaying stimulation of the muscle until the patient is detected to have the predetermined orientation.

The method and apparatus may further include facility to confirm that electrical stimulation results in muscle contraction, thereby providing information that may be used to indicate correct functioning of the system, and deliver an alarm in the event of suspected malfunction.

Electrical stimulation of the muscle may be delivered both for the purpose of providing muscle contraction for rehabilitation, and for the purpose of determining fusion frequency, thereby providing a diagnostic tool for identifying muscle fiber type and information about the progress of rehabilitation of the muscle.

V. BRIEF DESCRIPTION OF THE DRAWINGS

VI. DETAILED DESCRIPTION OF THE INVENTION

Apparatus and methods for rehabilitating a muscle are provided herein. The apparatus includes an electrode(s), a sensor(s), and a pulse generator. The electrodes(s) may be configured to be implanted in or adjacent to tissue and configured to stimulate the tissue at a stimulation frequency and at a level and duration sufficient to cause the muscle to contract. The sensor(s) may sense the muscle contraction and generate an output sensor signal based on the muscle contraction. The pulse generator includes a controller configured to receive the sensor signal and to adjust the stimulation frequency based on the sensor signal. Advantageously, the stimulation frequency may be adjusted to cause the muscle to contract at a fusion frequency where muscle contraction is smooth and continuous with minimal fatigue.

Figure 1:
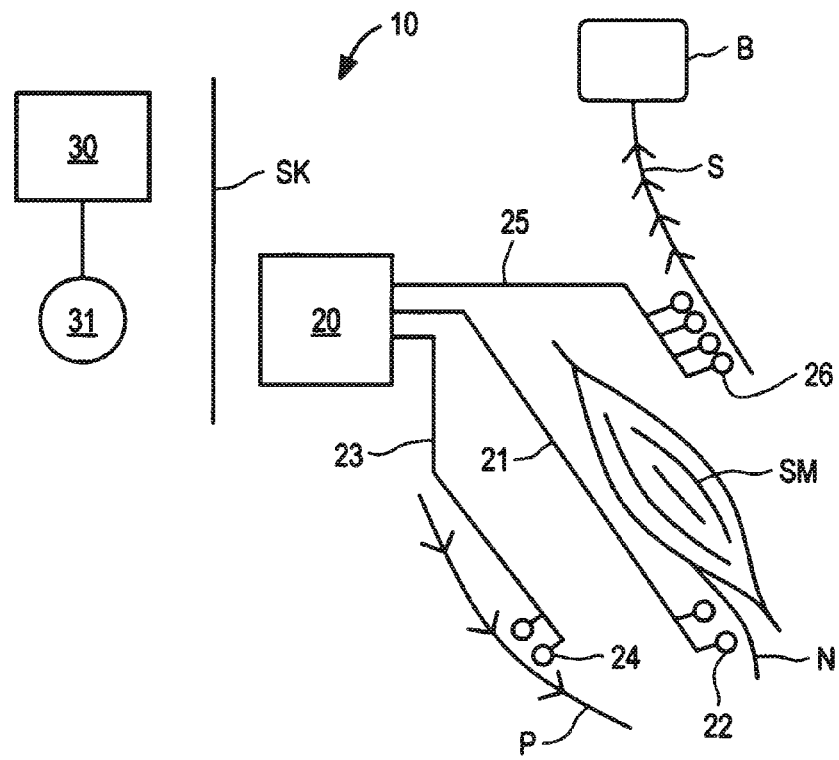
FIG. 1 is a schematic view of an exemplary embodiment of a stimulator system constructed in accordance with the principles of the present invention.

Referring to FIG. 1, an overview of an exemplary stimulator system constructed in accordance with the principles of the present invention is provided. In FIG. 1, components of the system are not depicted to scale on either a relative or absolute basis. Stimulator system 10 may include stimulator 20, which may be implantable or extracorporeal, and external control system 30. In the illustrated embodiment, software may be installed and run on a conventional laptop computer, and used by the patient's physician to program external control system 30 and/or to provide programming that is communicated by external control system 30 to stimulator 20. During patient visits, external system 30 may be coupled, either wirelessly or using a cable, to the physician's computer to download for review data stored on stimulator 20, or to adjust the operational parameters of the stimulator.

In FIG. 1 implantable stimulator 20 is a pulse generator connected to a plurality of electrode leads. Illustratively, electrode lead 21 is connected to electrode pair 22, which is situated close to or around a peripheral nerve N where the nerve enters skeletal muscle SM, which may be a multifidus muscle. Electrode pair 22 may deliver neuromuscular electrical stimulation ("NMES") pulses to nerve N that induce contraction of muscle SM to effect contraction of the muscle, and restoration of neural control and rehabilitation of the muscle, as described in the aforementioned U.S. Patent Application Publication No. 2008/0228241 to Sachs. Electrode lead 23 is illustratively disposed with electrode pair 24 adjacent or near to peripheral nerve P, such that electrical stimulation may be applied to achieve pain control in the region served by the peripheral nerves. Electrode lead 25 illustratively includes quadripolar electrode array 26, which is placed near spinal cord S in a manner well known to one skilled in the art to deliver Spinal Cord Stimulation therapy that reduces or blocks the transmission of pain signals to the patient's brain B. As would be apparent to one of ordinary skill in the art, various electrode locations and configurations would be acceptable, including the possibility of skin surface electrodes. The electrode(s) may be an array of a plurality of electrodes, or may be a simple single electrode where the electrical circuit is completed with an electrode placed elsewhere (not shown) such as a skin surface patch or by the can of an implanted pulse generator such as stimulator 20.

Implantable stimulator 20 may be controlled by, and optionally powered by, external control system 30, which communicates with stimulator 20 via antenna 31, which may comprise an inductive coil configured to transmit power and communicate information in a bidirectional manner across skin SIC. The technology for antenna 31 is well known to one skilled in the art and may include a magnet, a coil of wire, a longer range telemetry system (such as using MICS RF Telemetry available from Zarlink Semiconductor of Ottawa, Canada), or technology similar to a pacemaker programmer. Alternatively, coil 30 may be used to transmit power only, and separate radio frequency transmitters may be provided in external control system 30 and stimulator 20 for establishing directional data communication.

As will be appreciated by one of ordinary skill in the art, while stimulator 20 is illustratively implantable, stimulator 20 may be disposed external to a body of a patient on a temporary or permanent basis without departing from the scope of the present invention. In such an embodiment, stimulator 20 may be coupled to the electrodes by percutaneous leads. Alternatively, stimulator 20 and the electrodes may be completely external such that the leads are applied to the skin over a suitable location to elicit muscle contraction.

Figure 2:
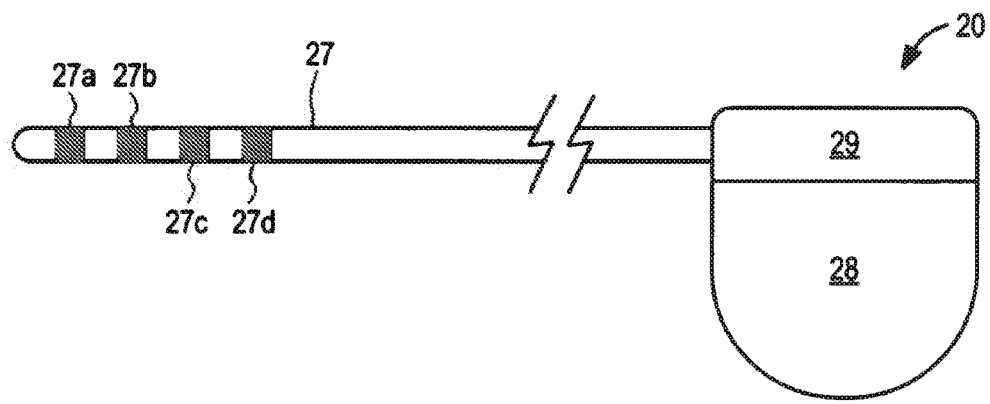
FIG. 2 is a side view of the implantable portion of the stimulator system of FIG. 1.

Referring now to FIG. 2, an exemplary embodiment of implantable stimulator 20 coupled to electrode lead 27 is described. As is common with other active implantable medical devices, the stimulator electronics are housed in a hermetically sealed metal housing 28. Housing 28 may comprise titanium or other biocompatible material, and includes connector block 29 that permits electrode lead 27 to be electrically coupled to the electronics within housing 28. While only one electrode lead 27 is shown coupled to connector block 29, it should be understood that multiple leads may connected to connector block 29, as shown in FIG. 1. Electrode lead 27 contains a plurality of electrodes 27a-27d that are configured to be implanted in or adjacent to tissue, such as a nerve, muscle, ligament, and/or joint capsule. Electrodes 27a-27d are configured to stimulate the tissue at a stimulation frequency and at a level and duration sufficient to cause the muscle to contract and may be ring electrodes, partial electrodes, segmented electrodes, nerve cuff electrodes placed around the nerve innervating the target muscle, or the like. The construction of electrode lead, the electrode design and manufacture, and connector block 29 are all well known to those skilled in the art. As will also be understood by one of skill in the art, an electrode lead may contain more or fewer than four electrodes.

Figure 3:
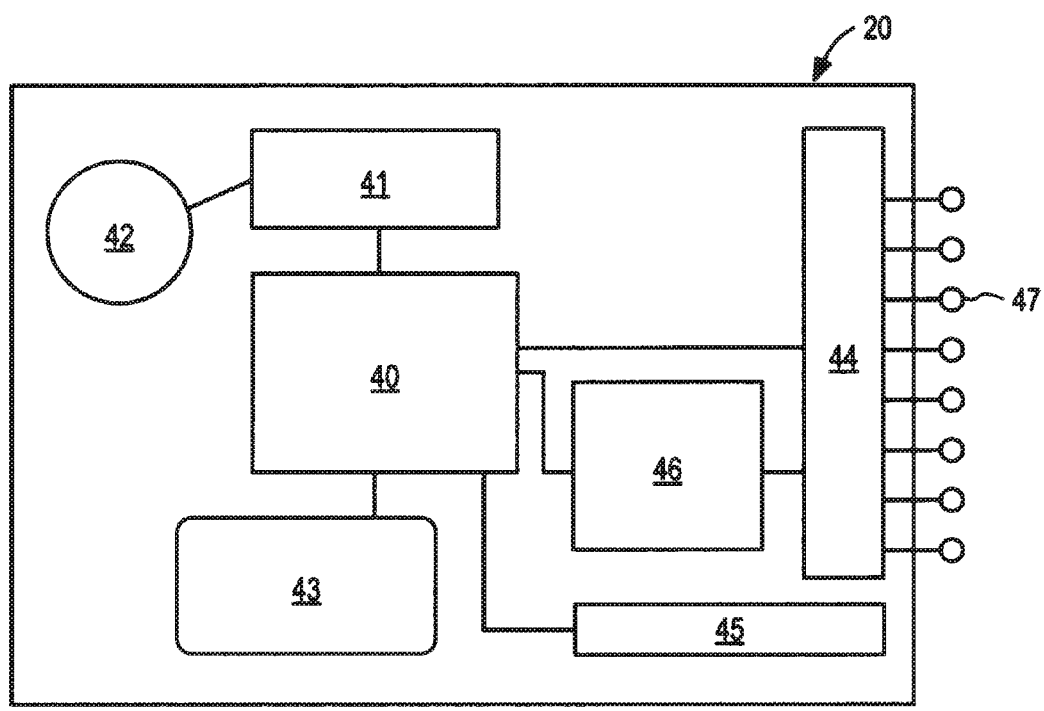
FIG. 3 is a generalized block diagram of the stimulator of FIG. 2.

With respect to FIG. 3, a generalized schematic diagram of the internal functional components of implantable stimulator 20 is now described. Stimulator 20 includes controller 40, telemetry system 41 coupled to antenna 42 (which may be inside or external to the hermetic housing), power supply 43, electrode switching array 44, system sensors 45, and therapeutic circuitry module 46. Electrode switching array 44 is selectably coupled to terminal array 47, which is housed in connector block 29 and enables stimulator 20 to be coupled to one or more electrode leads, as shown in FIG. 1.

Controller 40 is configured to control the internal functional components of implantable stimulator 20. Controller 40 may comprise a commercially available microcontroller unit including a programmable microprocessor, volatile memory, nonvolatile memory such as EEPROM for storing programming, and nonvolatile storage, e.g., Flash memory, for storing a log of system operational parameters and patient data. The memory of controller 40 may store program instructions that, when executed by the processor of controller 40, cause the processor and the functional components of implantable stimulator 20 to provide the functionality ascribed to them herein. Controller 40 is coupled to telemetry system 41 that permits transmission of energy and data between implantable stimulator 20 and external control system 30. Controller 40 also is coupled to therapeutic circuitry module 46 that provides any of a number of complimentary therapeutic stimulation, analgesic, feedback or ablation treatment modalities as described in detail below. Controller 40 further may be coupled to electrode switching array 44 so that any set of electrodes of the electrode leads may be selectably coupled to therapeutic circuitry module 46. In this way, an appropriate electrode set may be chosen from the entire selection of electrodes implanted in the patient's body to achieve a desired therapeutic effect. Electrode switching array 44 preferably operates at high speed, thereby allowing successive stimulation pulses to be applied to different electrode combinations. Controller 40 is configured to be programmable such that programming parameters may be adjusted including pulse amplitude (voltage or current), pulse width, stimulation rate, stimulation frequency, and electrode configuration. Additional sophistication of programming is possible as is commonly used for other types of pulse generators such as spinal cord or peripheral nerve stimulators.

Power supply 43 powers the electrical components of implantable stimulator 20, and may comprise a primary cell or battery, a secondary (rechargeable) cell or battery or a combination of both. Alternatively, power supply 43 may not include a cell or battery, but instead comprise a capacitor that stores energy transmitted through the skin via a Transcutaneous Energy Transmission System (TETs), e.g., by inductive coupling. Stimulator 20 may be programmed and/or controlled by, and may upload stored system and operational data to external control system 30 via telemetry system 41. In a preferred embodiment, power supply 43 comprises a lithium ion battery.

System sensors 45 may comprise one or more sensors that monitor operation of the systems of implantable stimulator 20, and log data relating to system operation as well as system faults, which may be stored in a log for later readout using the external control system. In one embodiment, system sensors 45 include one or more sensors configured to sense muscle contraction and to generate a sensor signal based on the muscle contraction. Controller 40 is configured to receive the sensor signal from system sensors 45 and to adjust the stimulation frequency based on the sensor signal. In one embodiment, system sensors 45 sense an increase or decrease in muscle movement and controller 40 increases or decreases the stimulation frequency to maintain smooth and continuous muscle contraction.

In a preferred embodiment, a sensor configured to sense muscle contraction is an accelerometer that senses acceleration of a muscle caused by muscle contraction. The accelerometer may be a 1-, 2- or 3-axis analog or digital accelerometer that may further determine whether the patient is active or asleep and to sense overall activity of the patient, which may be a surrogate measure for clinical parameters (e.g., more activity implies less pain), and/or a heart rate or breathing rate (minute ventilation) monitor, e.g., which may be obtained using one or more of the electrodes disposed on the electrode leads. The accelerometer may be used to determine the orientation of stimulator 20, and by inference the orientation of the patient, at any time. For example, after implantation, external control system 30 may be used to take a reading from the implant, e.g., when the patient is lying prone, to calibrate the orientation of the accelerometer. If the patient is instructed to lie prone during therapy delivery, then the accelerometer may be programmed to record the orientation of the patient during stimulation, thus providing information on patient compliance. In another embodiments, system sensors 45 include a pressure sensor, a movement sensor, and/or a strain gauge configured to sense muscle contraction and to generate a sensor signal based on the muscle contraction, and in a further embodiment, various combinations of at least one of an accelerometer, a pressure sensor, a movement sensor, and/or a strain gauge are included.

Sensors 45 may also include, for example, a humidity sensor to measure moisture within housing 28, which may provide information relating to the state of the electronic components, or a temperature sensor, e.g., for measuring battery temperature during charging to ensure safe operation of the battery. Data from the system sensors may be logged by controller 40 and stored in nonvolatile memory for later transmission to external controller 30 via telemetry system 41.

As will be appreciated by one of ordinary skill in the art, while system sensors 45 are illustratively disposed within housing 28 of stimulator 20, system sensors 45 may be placed in a variety of locations including within or adjacent to the tissue that is stimulated and/or in proximity to the muscle to be contracted and connected via a separate lead to stimulator 20. In other embodiments, sensors 45 may be integrated into one or more of the leads used for stimulation or may be an independent sensor(s) operatively coupled to stimulator 20 using, for example, radio frequency (RF) signals for transmitting and receiving data.

Implantable stimulator 20 illustratively includes one therapeutic circuitry module 46, although more circuitry modules may be employed in a particular embodiment depending upon its intended application, as described in the aforementioned U.S. Patent Application Publication No. 2011/0224665 to Crosby. Therapeutic circuitry module 46 may be configured to provide different types of stimulation, either to induce muscle contractions or to block pain signals in afferent nerve fibers, to monitor muscle contractions induced by stimulation and adjust the applied stimulation regime as needed to obtain a desired result, or to selectively and intermittently ablate nerve fibers to control pain and thereby facilitate muscle rehabilitation. As shown in FIG. 3, the therapeutic circuitry module is coupled to and controlled by controller 40.

Figure 4:
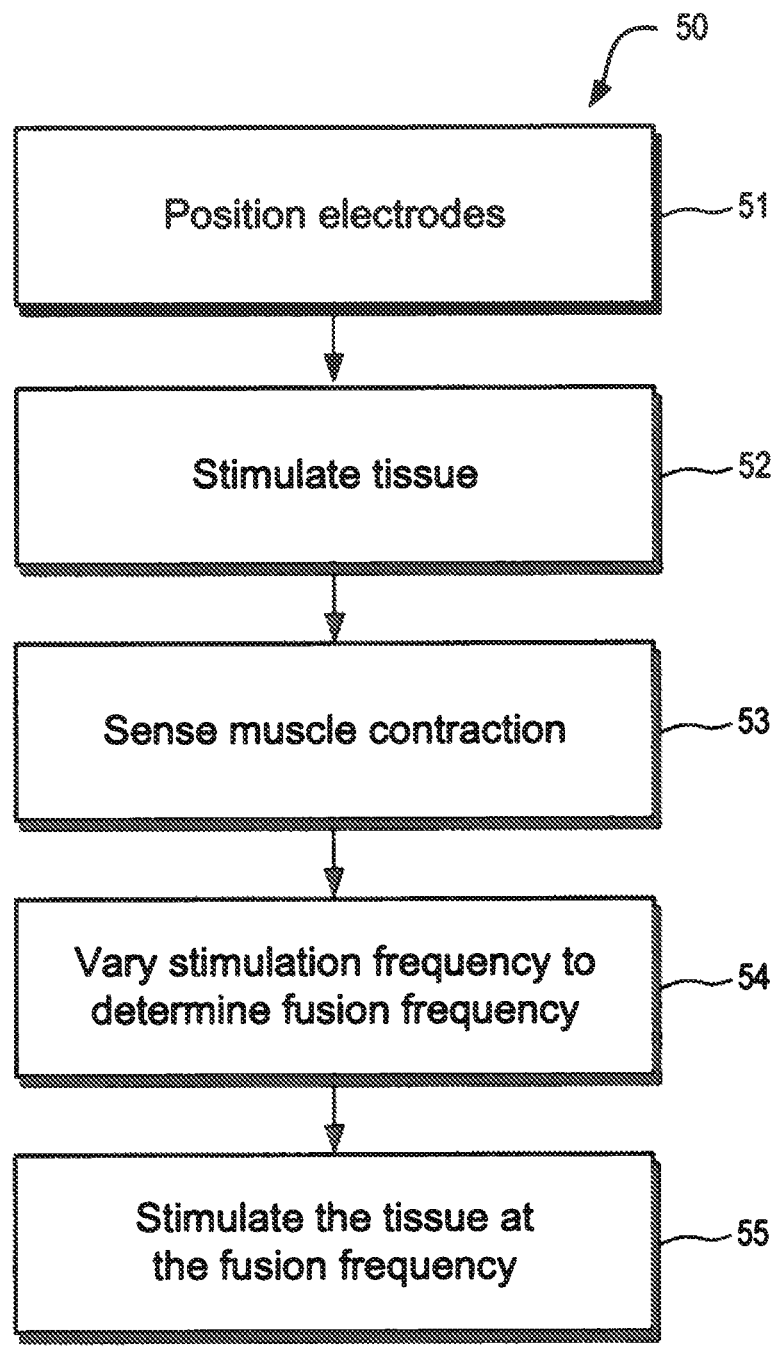
FIG. 4 is an exemplary method for rehabilitating a muscle in accordance with the principles of the present invention.

Referring to FIG. 4, exemplary method 50 for rehabilitating a muscle is provided in accordance with the principles of the present invention. At step 51, electrodes are positioned at a desired anatomical site such as placed on skin adjacent to tissue or implanted in or adjacent to tissue, e.g., muscle, nerve tissue, ligament, and/or joint capsule, using fluoroscopic, ultrasonic, anatomic, or CT guidance. In one embodiment, the electrodes are implanted in proximity to the medial branch of the dorsal ramus nerve proximal to where the nerve enters the multifidus muscle. The electrodes may be those described above with respect to stimulator system 10 of FIG. 1. A controller of a pulse generator, e.g., controller 40 of stimulator 20, may direct designated electrodes to stimulate the tissue at stimulation parameters such as pulse amplitude (voltage or current), pulse width, stimulation rate, and/or stimulation frequency at step 52. Preferably, the electrodes stimulate the tissue at a level and duration sufficient to cause a desired muscle, e.g., a multifidus muscle, to contract. One or more sensors, e.g., sensors 45, sense the muscle contraction caused by the stimulation at step 53. For example, in an embodiment where the sensors include an accelerometer, the accelerometer is configured to sense acceleration of the muscle caused by muscle contraction.

At step 54, the controller of the pulse generator may direct designated electrodes to stimulate the tissue at varied stimulation parameters, including at a varied stimulation frequency or time-wise sweep through a range of stimulation frequencies, based on the sensed muscle contraction. In one embodiment, the controller is configured to adjust the stimulation frequency based on the sensed muscle contraction to determine a fusion frequency of the muscle, as defined above. At step 55, the controller thereafter directs designated electrodes to stimulate the tissue at the fusion frequency. Advantageously, stimulating tissue at the fusion frequency will cause the muscle to contract such that muscle contraction is smooth and continuous. In addition, controller 40 may be configured to periodically or continuously sweep through a range of stimulation frequencies to follow potential changes in the fusion frequency during the course of the stimulation therapy.

Figure 5:
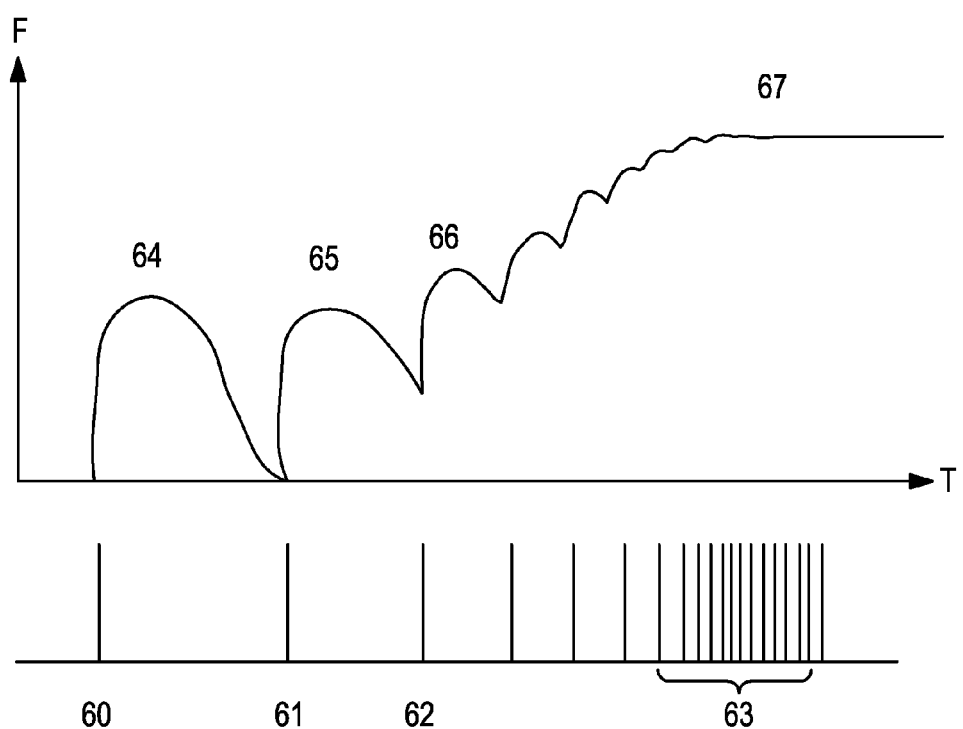
FIG. 5 shows a graph depicting an exemplary manner for determining the fusion frequency of a muscle.

Referring now to FIG. 5, a graph depicting an exemplary manner for determining the fusion frequency of a muscle is provided. The graph shows force generated in a stimulated muscle versus time as electrical stimulation pulses 60, 61, 62, and 63 are applied. Illustratively, a single stimulation pulse is applied at one time although the disclosure is not limited thereto. An isolated single stimulation pulse 60 applied with an electrode(s) will generate a twitch of rapidly rising contraction force 64 that then decays back to a force of zero. As used herein, a twitch refers to a contraction of a muscle.

A further stimulation pulse such as pulse 61 produces contraction force 65. If pulse 61 is followed by pulse 62 before the force generated by the muscle has decayed to zero, then the force produced by the muscle at contraction force 66 is higher than that produced by a single stimulation pulse at contraction force 65 because the new contraction force will be largely superimposed on the prior contraction, producing a summation of forces. As the time between stimulation pulses is decreased (i.e., the stimulation frequency is increased), the force continues to grow until the isolated twitch contractions fuse together to generate a smooth contraction of the muscle. The stimulation frequency at which that occurs is referred to as the fusion frequency illustrated as 63, generating a smooth force illustrated as contraction force 67. Stimulation at or above the fusion frequency is therefore expected to lead to smooth force generation. Stimulation at a rate significantly higher than the fusion frequency is expected to have a minimal effect on the strength or nature of contraction, but may have an adverse impact on fatigue of the muscle. Stimulation at a frequency higher than necessary to achieve the desired, e.g., maximum, force is energy inefficient and may adversely increase battery usage, which is an important consideration for an implantable device.

The strength of the contraction force further may be controlled by altering the intensity of the electrical stimulation— in general, higher stimulus intensity will elicit higher force. The mechanism for this is twofold. First, as the stimulation intensity is increased, then more motor units are recruited to contribute to the force generation. Second, as the intensity is increased, the force generated by each motor unit increases up to a physiologic limit.

Figure 6:
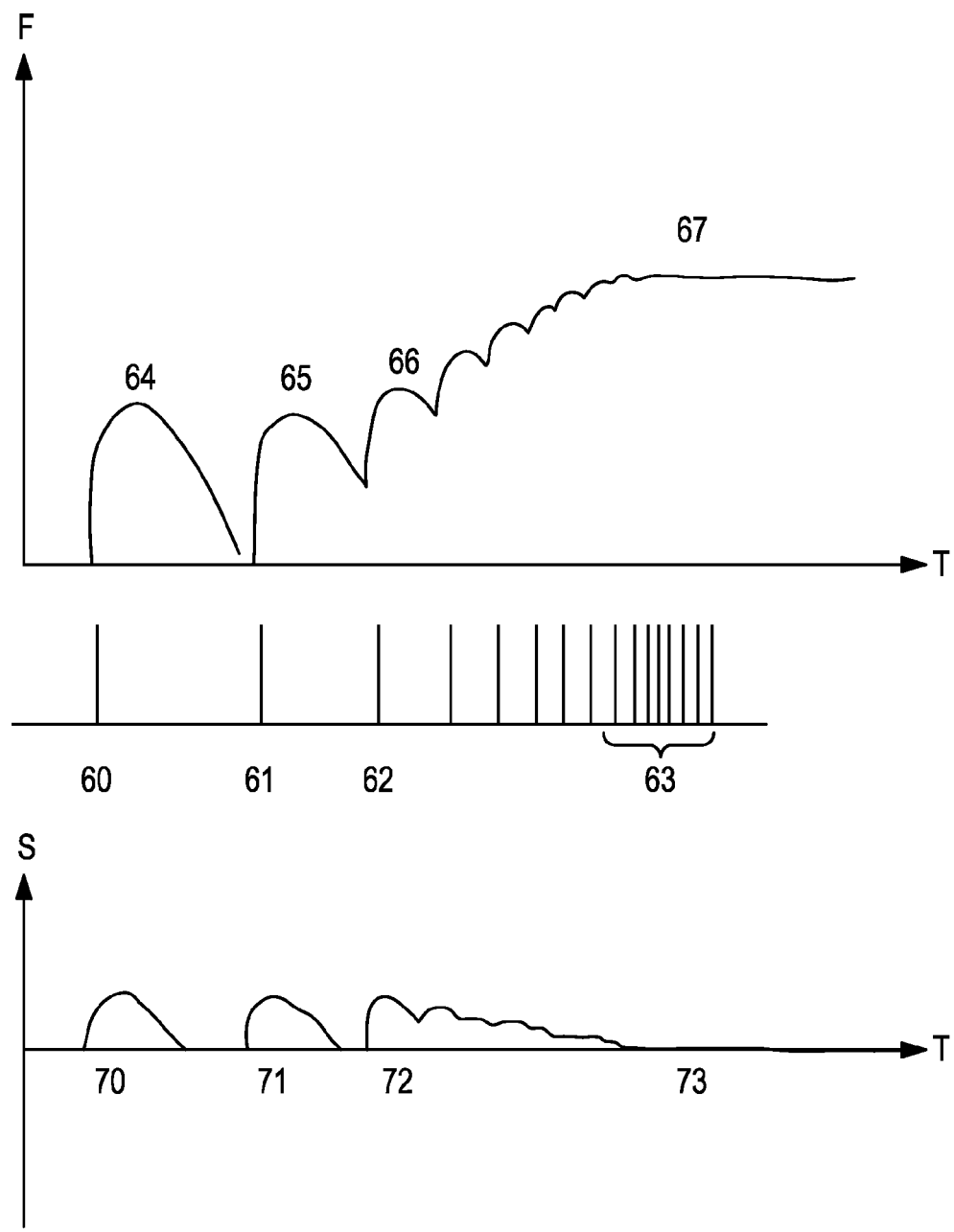
FIG. 6 shows a graph depicting an exemplary manner for determining the fusion frequency of a muscle using a sensor output together with the graph of FIG. 5.

Referring now to FIG. 6, a graph depicting an exemplary manner for determining the fusion frequency of a muscle using a sensor output is provided. The upper portion of FIG. 6 is the same as FIG. 5. The lower portion of FIG. 6 shows a conceptual output (S) of a sensor, illustratively an accelerometer, in response to stimulation over time. In a measurement mode, the pulse generator may deliver pulses at a predetermined minimum frequency, e.g., 2 Hz, to cause muscle contraction. Each time a pulse is delivered, the sensors sense the muscle contraction and generate a sensor signal based on the muscle contraction. The sensor signal is transmitted to electronics, e.g., controller 40, in the pulse generator which may process the sensor signal. Illustratively, contraction force 60 of the muscle, e.g., the multifidus, causes mechanical motion of the tissue surrounding the muscle, which will be sensed by the sensor, e.g., an accelerometer, as mechanical motion 70 of the sensor. Contraction forces 65 and 66 cause mechanical motions 71 and 72, respectively, sensed by the sensor. When contraction force 67 becomes constant, mechanical motion 73 approaches zero because the muscle contraction becomes substantially smooth and continuous, i.e., stimulation is achieved at the fusion frequency, shown as stimulation pulses 63. The system may continue to stimulate the muscle at or above the fusion frequency, determined by sensor output being near zero, and may continue to adjust stimulation parameters as the fusion frequency of the muscle changes over time during muscle rehabilitation.

It will be appreciated that the sensor responds to changes in muscle contraction—that is, when the muscle is completely relaxed, there is little to no sensor output signal. Likewise, when the muscle is smoothly and constantly contracted, there is little to no sensor output signal as there is little to no variation in muscle movement.

As the system increases the stimulation rate, the system monitors the signal from the sensor. The sensor signal may initially increase in amplitude as the stimulation rate increases as the force produced grows, and then may decrease in amplitude as the stimulation rate increases and the force of the twitches gradually become fused. When the signal from the sensor tends towards zero, it indicates that the muscle is contracting smoothly. In this process, the system is able to determine the fusion frequency of the target muscle. Signal processing, such as with a digital signal processor, may be used to enhance the accuracy and reliability of the detection algorithm. For example, the transition between twitch force generation and smooth force generation may be gradual, and the signal processing may generate a line of best fit to the amplitude of the sensor output versus frequency, and the line crosses the axis, (i.e., the variable force is zero) then this is defined as the fusion frequency.

In an alternative embodiment where a sensor, e.g., sensors 45, for sensing muscle contraction comprises a pressure sensor, a sensor signal similar to the sensor signal sent by an accelerometer indicating muscle contractions may be measured. If the pressure sensor is placed in or adjacent to the target muscle, then the sensor senses muscle force caused by contraction and generates a sensor signal based on the muscle contraction.

In an alternative embodiment, the sensor is continuously monitored by the controller during stimulation. During a session where the muscle is stimulated to contract (e.g., for between 10 and 30 seconds for each contraction with relaxation time between 10 and 60 seconds during a session of between 10 and 30 minutes), the stimulation rate is gradually reduced from the previously applied rate. When the sensor begins to detect changes in muscle force, then that is an indication that the stimulation is now lower than the fusion frequency. The stimulation frequency is then increased to a value slightly above the fusion frequency (to ensure smooth contraction), and the new value is recorded. In this manner, there is no need to sweep the frequency from a low (e.g., 2 Hz) stimulation rate to a high one, which may be advantageously more comfortable for the patient.

Measurement of the fusion frequency may be performed periodically, and the corresponding data may be stored within the pulse generator, e.g., on the memory of controller 40, for later read out by the physician, e.g., using external system 30. By use of data on the change in fusion frequency over time it is possible to monitor progress of the rehabilitation therapy. In one embodiment, the rehabilitation therapy is configured to stimulate the muscle for rehabilitation, and over time the rehabilitation will result in the conversion of Type II fast twitch fibers in the muscle to predominantly Type I slow twitch fibers. The fusion frequency for electrical stimulation of Type I slow twitch skeletal muscles is generally lower than Type II fast twitch skeletal muscles, reflecting the time that the twitch takes to decay. A fusion frequency for a slow twitch muscle may be approximately 10-15 Hz, and may be approximately 15-20 Hz for a fast twitch muscles. When the change in fusion frequency over time reaches a target minimum, e.g., as determined by a physician, it may be an indication that the rehabilitation therapy is complete, and therapy may be discontinued. If the fusion frequency does not change or changes but not to the target minimum value corresponding to Type I slow twitch fibers, then this may be an indication that the therapy is not working as intended, and adjustments, e.g., repositioning of the electrodes, may be necessary. In this manner, the invention disclosed herein provides the physician a manner to monitor progress of rehabilitation of a muscle.

Figure 7:
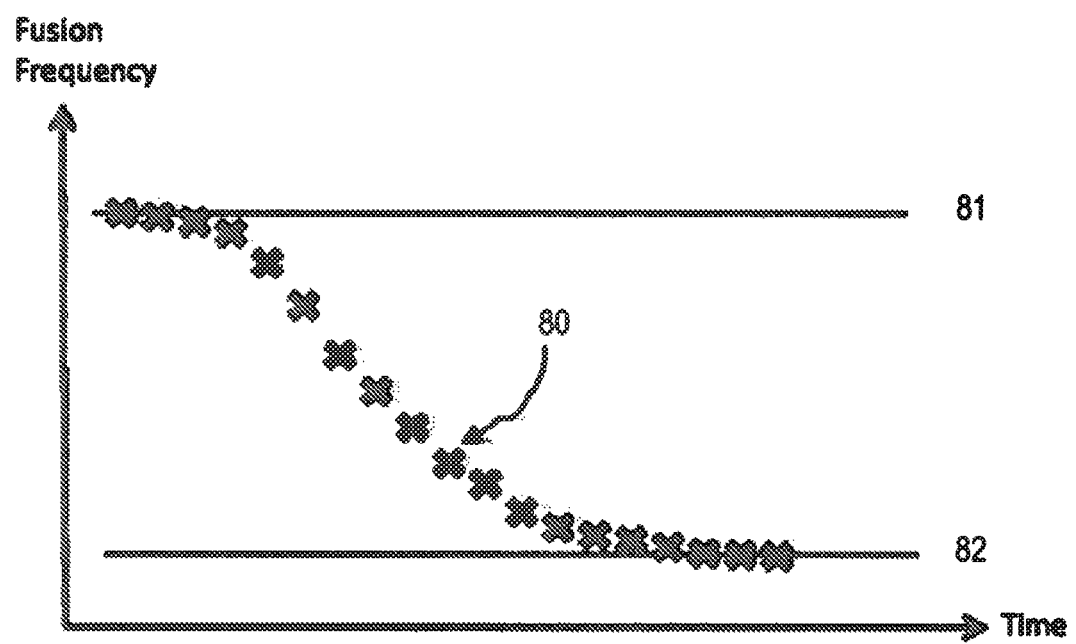
FIG. 7 shows a graph of fusion frequency versus time depicting conversion from Type II fast twitch fibers in the muscle to predominantly Type I slow twitch fibers.

Referring now to FIG. 7, a graph depicting conversion from Type II fast twitch fibers in the muscle to predominantly Type I slow twitch fibers is provided. Fusion frequency measurements 80 may be transmitted from the memory of the pulse generator and logged, e.g., in external system 30, at regular intervals, such as once per week. Line 81 shows the determined fusion frequency at the beginning of therapy where the fusion frequency is that of Type II fast twitch fibers. As the therapy progresses, the fusion frequency begins to decrease as the mixture of Type II fast twitch and Type I slow twitch fibers change. Eventually, the fusion frequency stabilizes at a lower value where the fusion frequency is that of predominantly Type I slow twitch fibers, represented by line 82. Once the measured fusion frequency has stabilized, the therapy may be discontinued, as the muscle has converted to predominantly Type I slow twitch fibers, and thus has been rehabilitated.

The pulse generator may be programmable and the memory of the controller, e.g., controller 40, may store program instructions that, when executed by the processor of the controller, cause the processor and the functional components of the pulse generator to provide the functionality ascribed to them herein. The controller may be programmed with an algorithm that automatically adjusts the stimulation parameters in response to change in the measured fusion frequency. For example, as the fusion frequency declines, the algorithm adjusts the maximum stimulation rate during normal therapy sessions to be slightly above the fusion frequency. In this manner, the stimulation rate is kept as low as possible consistent with the desired therapy, which helps to preserve battery life of an implantable pulse generator, and may result in more comfortable sensations and less fatigue for the patient.

The pulse generator also may be programmed to measure the muscle response to stimulation to verify correct operation—that is, to verify that electrical stimulation actually results in muscle contraction. In some circumstances, the magnitude of the electrical signal required to cause contraction may alter over time, for example, if the electrode moves or as fibrous tissue grows to surround the electrodes thereby leading to less efficient energy coupling to the target tissue, e.g., nerve, muscle, ligament, joint capsule. The pulse generator may deliver a pulse, and the controller determines the amplitude of the sensor signal from the sensor. If the muscle response is below a preprogrammed threshold then the controller increments the stimulation strength and listens to the muscle response measured by the sensor(s). The process may be continued incrementally, increasing or decreasing the stimulation strength up to or down to a pre-programmed maximum or minimum value. If the controller directs the electrode(s) to increase the stimulation strength to a pre-programmed maximum value and there is still no response or an inadequate response, this may indicate a fault in the system such as a lead dislodgement, and an alarm may be generated and optionally transmitted to the external system.

A pressure sensor also may be incorporated into the system, as explained above, and placed in a location where it may sense the force generated by contraction of the muscle to verify contraction of the muscle such that the controller may adjust the amplitude of stimulation to an appropriate level, using the same steps as described above. The pressure sensor may be used to track if the therapy is working as intended, by measuring the force of contraction of the muscle in response to a fixed amplitude of stimulation, as well as measuring the force of contraction in response to stimulation with different parameters, e.g., intensity pulse width or stimulation rate. In this manner, the system may automatically adjust the stimulation parameters to ensure efficient capture of the muscle, and to allow delivery of optimal stimulation.

In addition, other sensors may be provided to confirm that the patient is lying with a preferred orientation, e.g., lying down, before initiating stimulation therapy. In this way, controller 40 may be assured that the stimulation therapy is conducted under consistent conditions.

The apparatus described may be used to monitor the progress of other types of rehabilitative therapy such as physiotherapy, or combination therapies such as physiotherapy used in conjunction with NMES for rehabilitation. That is, the apparatus described may be used for therapeutic electrical stimulation, for monitoring progress of other therapy or combination therapies, or both.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. An apparatus for rehabilitating a muscle, the apparatus comprising:
   one or more electrodes configured to be positioned in or adjacent to tissue and configured to stimulate the tissue at a stimulation frequency and at a level and duration sufficient to cause the muscle to contract;
   one or more sensors configured to sense the muscle contraction and to generate a sensor signal based on the muscle contraction;
   a pulse generator operatively coupled to the one or more electrodes, the pulse generator having a controller configured to receive the sensor signal,
   wherein the controller is configured to automatically adjust the stimulation frequency based on the sensor signal to or above a measured fusion frequency and to cause the one or more electrodes to stimulate the tissue at or above the measured fusion frequency so as to induce smooth continuous contraction of the muscle, the controller further configured to automatically adjust the stimulation frequency over a course of a therapy to reflect changes in the measured fusion frequency resulting from prior therapeutic stimulation sessions.

2. The apparatus of claim 1, wherein the one or more electrodes are configured to be implanted in or adjacent to a nerve.

3. The apparatus of claim 1, wherein the muscle comprises a multifidus muscle.

4. The apparatus of claim 1, wherein the one or more sensors comprise at least one of an accelerometer, a pressure sensor, a movement sensor, a strain gauge, or any combination thereof.

5. The apparatus of claim 1, wherein the one or more sensors are disposed within a housing of the pulse generator.

6. The apparatus of claim 1, wherein the one or more sensors are disposed within or adjacent to the tissue.

7. The apparatus of claim 1, wherein the pulse generator is configured to be implanted in a body.

8. The apparatus of claim 1, wherein the pulse generator is configured to be disposed external to a body.

9. The apparatus of claim 1, wherein the controller is programmed to automatically adjust one or more of pulse amplitude, pulse width, stimulation rate, and electrode configuration.

10. The apparatus of claim 1, wherein the muscle is associated with local segmental control of a spine.

11. A method for rehabilitating a muscle, the method comprising:
    positioning one or more electrodes in or adjacent to tissue;
    using the one or more electrodes to stimulate the tissue at a stimulation frequency and at a level and duration sufficient to induce smooth and continuous contraction of the muscle;
    sensing the muscle contraction;
    automatically adjusting the stimulation frequency based on the sensed muscle contraction to or above a measured fusion frequency;
    stimulating the tissue at or above the measured fusion frequency using the one or more electrodes to maintain smooth and continuous muscle contraction; and
    automatically adjusting the adjusted stimulation frequency over a course of a therapy to reflect changes in the measured fusion frequency resulting from prior therapeutic stimulation sessions.

12. The method of claim 11, further comprising automatically adjusting one or more of pulse amplitude, pulse width, stimulation rate, and electrode configuration.

13. The method of claim 11, wherein the muscle comprises a multifidus muscle.

14. The method of claim 11, wherein the tissue comprises a medial branch of the dorsal ramus nerve.

15. The method of claim 11, wherein sensing the muscle contraction comprises sensing the muscle contraction using an accelerometer, a pressure sensor, a movement sensor, a strain gauge, or any combination thereof.

16. The method of claim 11, wherein positioning the one or more electrodes comprises implanting the one or more electrodes in or adjacent to the tissue.

17. The method of claim 11, positioning the one or more electrodes comprises placing the one or more electrodes on skin adjacent to the tissue.

18. The method of claim 11, wherein sensing the muscle contraction comprises sensing the muscle contraction using an accelerometer.

19. The method of claim 11, wherein adjusting the stimulation frequency comprises changing the stimulation frequency based on the sensed muscle contraction to convert Type II fast twitch fibers in the muscle to predominantly Type I slow twitch fibers.

20. The method of claim 11, further comprising:
    providing a sensor configured to detect a predetermined orientation of a patient's body; and
    delaying stimulation of the muscle until the patient is detected to have the predetermined orientation.

21. The method of claim 11, wherein sensing the muscle contraction comprises sensing an increase or decrease in muscle movement; and
    wherein adjusting the stimulation frequency comprises increasing or decreasing the stimulation frequency to maintain smooth and continuous muscle contraction.

* * * * *